United States Patent
Radmand

[19]

[11] Patent Number: 6,117,110

[45] Date of Patent: Sep. 12, 2000

[54] CATHETER NEEDLE SAFETY DEVICE AND METHOD OF USING SAME

[76] Inventor: Reza Radmand, 15720 Ventura Blvd., Suite 609, Encino, Calif. 91436

[21] Appl. No.: 09/277,292

[22] Filed: Mar. 26, 1999

[51] Int. Cl.[7] .................................................. A61M 5/00
[52] U.S. Cl. ........................... 604/162; 604/171; 604/263
[58] Field of Search .................................... 604/158, 162, 604/164, 171, 198, 263, 264

[56] References Cited

U.S. PATENT DOCUMENTS

| | | |
|---|---|---|
| 4,834,718 | 5/1989 | McDonald . |
| 4,846,805 | 7/1989 | Sitar . |
| 4,846,811 | 7/1989 | Vanderhoof . |
| 4,850,996 | 7/1989 | Cree . |
| 4,872,552 | 10/1989 | Unger . |
| 4,944,725 | 7/1990 | McDonald . |
| 5,000,740 | 3/1991 | Ducharme et al. ...................... 604/162 |
| 5,531,713 | 7/1996 | Mastronardi et al. ............... 604/171 X |
| 5,545,146 | 8/1996 | Ishak ................................... 604/164 X |
| 5,562,631 | 10/1996 | Bogert . |
| 5,569,202 | 10/1996 | Kovalic et al. . |
| 5,569,217 | 10/1996 | Luther . |
| 5,573,510 | 11/1996 | Isaacson ................................... 604/158 |
| 5,611,781 | 3/1997 | Sircom et al. . |
| 5,683,368 | 11/1997 | Schmidt . |
| 5,718,688 | 2/1998 | Wozencroft . |
| 5,735,823 | 4/1998 | Berger . |
| 5,769,827 | 6/1998 | DeMichele et al. . |
| 5,795,339 | 8/1998 | Erskine ................................... 604/264 |

*Primary Examiner*—John D. Yasko
*Attorney, Agent, or Firm*—Hogan & Hartson, LLP

[57] ABSTRACT

A safety apparatus and method of use for a catheter and needle combination. An automatic sheathing system protects clinical personnel from accidental needle sticks after withdrawing the needle from a patient. The device consists of a clear, plastic needle guard with a flanged-end opening that allows a polytetrafluoroethylene catheter and needle to protrude (covered by a protective cap), but prevents the hubs of each from passing outside. For venipuncture, the cap is removed and the needle tip passes through the catheter. The user, employing a one-handed method, punctures the skin of the patient with the needle tip and locates a vein. The needle is then withdrawn as the catheter slides over the needle tip into the vein. A needle guard, including a one-way detent and a restraining ledge, captures the needle hub when the needle is withdrawn. At all times during the withdrawal process the needle guard encloses the needle tip. As the guard captures the needle, the catheter continues to be gripped by a flanged end of the guard. When the user is ready to release the catheter, the guard is squeezed near the flanged end expanding the opening and allowing the user to remove the guard leaving the catheter in place.

19 Claims, 1 Drawing Sheet

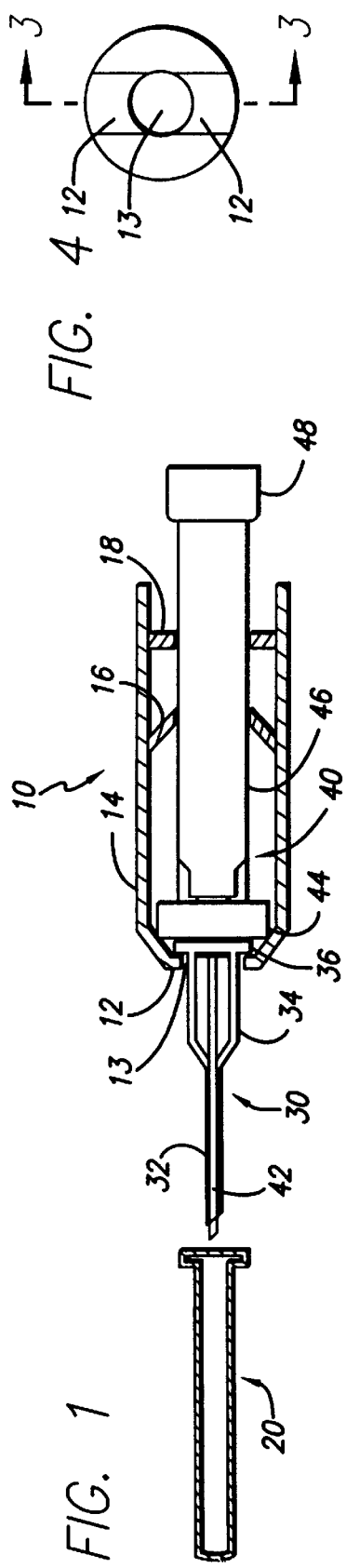
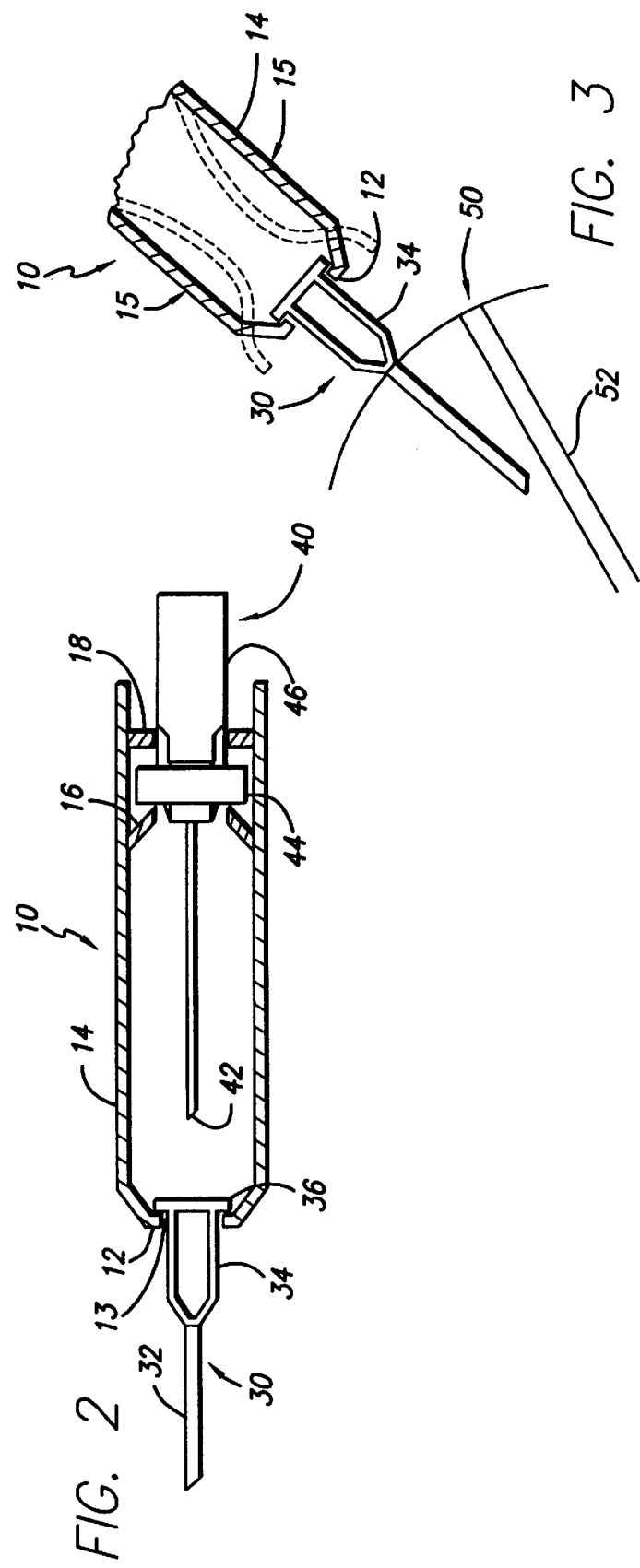

CATHETER NEEDLE SAFETY DEVICE AND METHOD OF USING SAME

BACKGROUND OF THE INVENTION

1. Field of the Invention

The present invention relates generally to medical devices, and more particularly to a safety device to protect medical personnel from accidental puncture by a needle by using a protective sheath to surround the needle tip after a catheter is inserted into a patient and the needle is withdrawn.

2. Description of Related Art

Catheters and safety needle devices are well known in the art. These devices have been developed because it is necessary to protect against the possibility of accidental needle stick. Various life-threatening diseases such as hepatitis and acquired immune deficiency syndrome (AIDS) make needle protection a serious matter. Needles and syringes are used for a variety of purposes in a clinical environment such as injecting drugs or withdrawing blood. More recently, it has become common practice to use a needle to aid in the insertion of a flexible intravenous (IV) catheter into a vein. IV catheters are used to alleviate the trauma of repeated injections and the discomfort associated with leaving a needle in a patient for an extended period. There are two types of IV catheters: through-the-needle catheters, in which a catheter is threaded through the needle into the vein of a patient, and over-the-needle catheters, in which a catheter is placed over the needle and inserted simultaneously with the needle, staying in the vein when the needle is withdrawn. The needle is used to puncture the skin and locate the vein; thereafter the catheter is slid over the needle and into the vein, staying in position so that periodic administration of fluids, drugs, transfusions, and collecting of blood samples is possible.

The process of inserting an over-the-needle catheter into a vein usually requires the needle tip to be exposed once withdrawn from the patient. Often times, the needle will be set down while other urgent procedures are attended to, and taken to a sharps container at a later time. In all such needle applications, the tip of the needle is exposed from the time it is withdrawn from the patient up until the time it is placed in a sharps container. Therefore, there is a need for a protective device of some kind to fit over the needle to protect against accidental exposure of medical personnel to pathogens left on the needle from the patient's blood.

Much of the prior art in this field requires an extra step to be performed by the user to ensure protection from the needle tip. For example, U.S. Pat. No. 5,569,217 to Luther is directed to a percutaneous port catheter assembly and method of use. A protective casing is slidably mounted within the housing. The casing is mounted in a manner that allows the casing to pass axially through the passage orifices of the base. At the proximal end of the casing, a protective cap is provided which has an outer surface that is used to press the casing through the housing. By requiring the user to push the casing through the housing after removal of the needle, however, there exists the possibility that the user will forget or neglect to do so, thereby rendering the safety device useless.

Some prior art, thus, addressed the problem by implementing automatic sheathing systems. One of the first to do so was McDonald in U.S. Pat. No. 4,944,725. This patent is directed to an automatic covering system for an intravenous catheter. The system includes a needle, handle means for manipulating the needle, a protective housing means to cover the needle, a latch means to prevent unwanted movement of the needle, and locking means to lock the catheter to the housing for insertion. An over-the-needle catheter is introduced into the patient, and the needle is withdrawn into the protective housing without the needle being exposed. Latch means, in the form of latching fingers formed on diametrically opposite sides of the housing, and an annular latch detent formed on the shell, eventually lock together to permanently trap the needle tip inside the passage.

U.S. Pat. No. 5,769,827 to DeMichele et al. improved upon the McDonald device by adding a cap to provide additional safety. The protective cap is frusto-conical and has a larger somewhat cylindrical end opposite a narrower cylindrical end that is mountable on the narrowed cap-mounting hub on the needle housing. The catheter hub mounts on the catheter mount and is retained in place by radially extending arms. The larger end of the cap has an internal radial rib and the handle housing has a mating radial detent on the needle end of the handle housing. The larger end of the cap is mounted on the needle end so that the cap's internal rib abuts the radial detent in the housing.

While the automatic sheathing devices were an improvement on the needle protectors that required an additional step after withdrawal of the needle, they are still deficient in that they are complex, involving numerous steps to operate, impractical in their design, and costly to manufacture. Thus, there exists a need for a simple, easy to use, and cost-effective automatic sheathing device to protect against accidental needle stick.

SUMMARY OF THE INVENTION

Accordingly, the present invention provides an angiocatheter protective needle guard to protect clinical personnel from exposure to the tip of a withdrawn needle. The needle guard consists of a clear protective guard sized to fit over a polytetrafluoroethylene (PTFE) catheter and needle combination. The protective guard has a gripping system, which is capable of trapping the hub of the needle at one end and gripping the hub of the PTFE catheter at the other. The catheter fits over the needle, and the hub of each is inside the device before insertion. A cap, which fits over the catheter, is removed and the needle tip is used to puncture the skin of a patient for insertion into a vein. Following insertion, the needle can be used to deliver medication to the patient or withdraw blood samples from the patient. The catheter then slides over the needle tip and into the vein. At this point, the needle is withdrawn into the protective guard of the present invention so that the guard covers the needle tip. The needle is withdrawn until the needle hub passes a first set of slanted projections (a one-way detent), which allow movement only in the direction toward the user (e.g., movement of the needle out of and away from the PTFE sheath). At this point the needle hub is trapped between the one-way detent and a restraining ledge positioned just above the one-way detent. Because the distance from the one-way detent to the flanged end of the needle guard is greater than the distance from the distal tip of the needle to the needle hub, the needle is completely within the guard. This containment system keeps the needle from sliding downward toward the patient or upward toward the user, thus avoiding any possibility of exposure to the needle tip. While the needle is withdrawn from the patient and locked into place, the flanged end of the guard continues to grip the catheter hub. The guard is then squeezed by the user to release the catheter hub by spreading the flanges apart. Before the needle hub is trapped by the containment system, the hub prevents the needle guard from being squeezed to open the flanges. The needle guard with the needle fully enclosed and secured therein can be safely disposed of in a sharps container. The inventive needle guard, thus, is a very user friendly device that is inexpensive to manufacture due to its simplicity while still providing maximum safety by preventing accidental needle puncture from a contaminated needle.

These and other features and advantages of the present invention will become more apparent to those skilled in the art when taken with reference to the following more detailed description of the preferred embodiments of the invention in conjunction with the accompanying drawings.

BRIEF DESCRIPTION OF THE DRAWINGS

FIG. 1 is a cross-sectional view of a fully assembled catheter insertion device surrounded by the needle guard of the present invention before insertion into a patient.

FIG. 2 is a cross-sectional view of the catheter insertion device after the needle has been withdrawn and secured inside the needle guard.

FIG. 3 is a cross-sectional view of a catheter inserted into a vein before the needle guard has been removed with the flanged end shown in a released position in phantom.

FIG. 4 is a view of the flanged end of the needle guard of the present invention.

DETAILED DESCRIPTION OF THE PREFERRED EMBODIMENTS

The present invention satisfies the need for a safety apparatus and method of use for medical procedures involving needles that is easy to use and cost-effective. More particularly, the present invention provides a simple automatic needle guard system to protect the user from exposure to a contaminated needle. The guard system is contemplated for use with catheter insertion procedures but will work for any procedure involving a needle. In the detailed description that follows, it should be appreciated that like reference numerals are used to describe like elements illustrated in one or more of the figures.

Turning now to FIG. 1, a cross-sectional view of a needle guard system 10 is shown surrounding a catheter 30, which is placed over a needle 40. A cap 20 is placed over the catheter 30 for safety purposes but is removed prior to actual use. The catheter 30 includes a catheter tip portion 32, a catheter body 34 and a catheter hub 36. As shown in FIG. 1, the catheter hub 36 is abutted to a needle hub 44 when a needle tip 42 is within the catheter 30. The needle 40 also includes a body 46 and a removable stopper or syringe 48. A needle guard 14 is cylindrical in shape and surrounds both the catheter 30 and the needle 40, holding both by a flanged end 12 located at a distal end of the guard 14. The flanged end 12 prevents the catheter hub 36 and the needle hub 44 from slipping outside of the guard 14 since the opening in the flanged end 12 is smaller than either hub. Located toward the proximal end, or base, of the guard 14, is a containment system for the needle 40 after it is withdrawn from the patient. The containment system consists of a flexible one-way detent 16 and a restraining ledge 18. The flexible one-way detent 16 can be made of any resilient plastic material so that the needle 40 can pass while moving toward the user, but once the needle hub 44 passes through the one-way detent 16, it is prevented from moving back toward the patient. The angle of the one-way detent 16 prevents back movement of the needle. The restraining ledge 18 is also formed from the plastic of the needle guard 14 and restricts farther movement of the needle 40 toward the user.

Coupled with the fact that needle guard 14 is longer than the needle 40, the guard 14 locks the needle 40 in place after it has been withdrawn from the patient and safely keeps the needle tip 42 enclosed for disposal. Ideally, a plastic with the correct properties is selected for the entire guard 14.

When the catheter 30 is to be inserted into a patient, the cap 20 is removed, and the needle tip 42 punctures the patient's skin 50 (FIG. 3) and enters a vein 52 (FIG. 3). The needle 40 is manipulated using the conventionally safe one-handed method. Once the needle 40 is positioned within the vein 52, the flexible catheter 30 is pressed along the needle 40 to also enter the vein 52. The needle 40 can then be used to inject drugs into the vein 52 or to withdraw blood from the vein 52. Alternatively, the needle 40 can simply be withdrawn into the guard 14 immediately after venipuncture, while the catheter 30 remains inside of vein 52. Withdrawing the needle 40 also requires only one hand of the user so that the other hand can be kept safely away from any needle stick.

FIG. 2 shows a cross-sectional view of the system 10 after the needle 40 has been withdrawn into the containment system. The needle hub 44 is restricted from moving in either direction because the needle hub 414 is blocked in the distal direction by one-way detent 16 and blocked in the proximal direction by the restraining ledge 18. As shown in FIG. 2, the needle tip 42 is safely enclosed by the needle guard wall 14 and is a significant distance from the flanged end 12. The catheter hub 36 is prevented from moving outside the needle guard 14 by the flanged end 12.

FIG. 3 shows a cross-sectional view of the system 10 after the catheter 30 has been inserted into the vein 52 and the needle 40 has been withdrawn. The catheter 30 can be released from the needle guard 14 by squeezing at the distal points 15. Squeezing opposite sides of the guard 14 at distal points 15 causes the flanges 12 to expand outwardly (shown in phantom) substantially increasing the size of the end opening 13.

FIG. 4 shows an end view of the structure of the present invention before the catheter 30 is released. In a preferred embodiment the flanges 12 represent two fairly narrow strips cut into the plastic at that end of the needle guard 14. It will be apparent to those of skill in the art that other numbers and arrangements of flanges 12 could be readily implemented. What is important is that the flanges 12 be manipulable to release the catheter 30. The user can then easily remove the catheter 30 from the needle guard 14, leaving it in place inside the patient. Once the distal points 15 are released by the user, the flanges 12 close. Significantly, an inspection of FIG. 1 will show that the needle hub 44 can be configured to prevent the squeezing of points 15. That is, until the needle hub 44 has been withdrawn beyond the one-way detent 16, the needle guard 14 will not buckle inward sufficiently to open the flanges 12 when squeezed.

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

I claim:

1. An automatic sheathing system, comprising:
   an introducing catheter including a catheter tip and a catheter hub;
   a needle including a needle tip, and a needle hub, wherein said needle is sized to fit within said introducing catheter; and,
   a needle sheath disposed around said introducing catheter and said needle, wherein said sheath further comprises a flanged end configured for releasably gripping said catheter hub, and wherein said catheter hub is released when said flanged end is squeezed.

2. The automatic sheathing system of claim 1, wherein said introducing catheter is made of polytetrafluoroethylene.

3. The automatic sheathing system of claim 1, further comprising a catheter cap covering said catheter tip.

4. The automatic sheathing system of claim 1, wherein the length measured from a distal end of said needle tip to said needle hub is greater than the length measured from a distal end of said catheter tip to said catheter hub.

5. The automatic sheathing system of claim 1 further comprising a syringe.

6. The automatic sheathing system of claim 1, wherein said sheath further comprises a one-way detent allowing movement of said needle hub past said detent in a direction away from said flanged end and preventing movement of said needle hub past said detent in a direction towards said flanged end.

7. The automatic sheathing system of claim 6, wherein said flanged end can release the catheter hub only after the needle hub has moved past the one-way detent.

8. The automatic sheathing system of claim 6, wherein the distance between said opening of said flanged end and said one-way detent is greater than the distance between a distal end of said needle tip and said needle hub.

9. An automatic sheathing system, comprising:
   means for contacting an internal vein of a patient;
   means for puncturing the skin of said patient and introducing said means for contacting into said vein; and
   means for sheathing said means for puncturing, wherein said sheathing means further comprises trapping means for trapping said means for puncturing within said sheathing means and means for releasably gripping said means for contacting, wherein said means for releasably gripping can release said means for contacting when said means for sheathing are squeezed after said means for puncturing has been trapped by said means for trapping.

10. The automatic sheathing system of claim 9, wherein said means for contacting comprises an introducing catheter including a catheter tip and a catheter hub.

11. The automatic sheathing system of claim 9, wherein said contact means is made of polytetrafluoroethylene.

12. The automatic sheathing system of claim 9, wherein said means for puncturing comprises a needle including a needle tip, a needle hub and a needle body, wherein said needle tip is disposed within said contact means for contacting.

13. The automatic sheathing system of claim 9, wherein said sheathing means further comprises a flanged end for releasably gripping said means for contacting.

14. The automatic sheathing system of claim 13, wherein said means for sheathing comprises a one-way detent and a ledge for trapping said means for puncturing when said means for puncturing is moved through said means for sheathing.

15. The automatic sheathing system of claim 14, wherein said one-way detent is made of a resilient plastic material.

16. A method for the automatic sheathing of a needle after inserting a catheter into a patient, wherein said catheter includes a catheter tip and a catheter hub, wherein said needle includes a needle tip, a needle hub, wherein said needle tip is disposed within said catheter tip, wherein a needle sheath is used to prevent accidental sticks from said needle, wherein said needle sheath includes a trapping mechanism for trapping said needle hub so that said needle tip is contained within said sheath and wherein said needle sheath includes a flanged end for releasably gripping said catheter hub so that said catheter hub can be released when said needle hub is trapped by the trapping mechanism, the method comprising the steps of:
   pushing said needle tip through said catheter tip so that said needle tip forms a puncture in the skin of a patient;
   inserting said catheter into said puncture by sliding said catheter tip over said needle tip;
   withdrawing said needle into said needle sheath until said needle hub is trapped within said trapping system;
   pressing inward on opposing sides of said sheath near said flanged end, thereby releasing said hub of said catheter; and
   removing said sheath with said needle contained inside from said catheter hub.

17. The method of claim 16, wherein said trapping system comprises a one-way detent, wherein said needle hub is trapped within said sheath upon passing through said one-way detent.

18. The method of claim 16, further comprising withdrawing a blood sample from said patient into said needle before said catheter is inserted.

19. The method of claim 16, further comprising injecting a fluid from said needle into said patient before said catheter is inserted.

* * * * *